United States Patent
Cecchi et al.

(10) Patent No.: US 7,915,034 B2
(45) Date of Patent: Mar. 29, 2011

(54) APPARATUS AND METHOD FOR CULTURING OOCYTES, EMBRYOS, STEM CELLS AND CELLS

(75) Inventors: Michael D. Cecchi, Madison, CT (US);
Jacques Cohen, New York, NY (US);
Tim Schimmel, Randolph, NJ (US)

(73) Assignee: Genx International, Guilford, CT (US)

( * ) Notice: Subject to any disclaimer, the term of this patent is extended or adjusted under 35 U.S.C. 154(b) by 1306 days.

(21) Appl. No.: 11/477,099

(22) Filed: Jun. 29, 2006

(65) Prior Publication Data
US 2008/0003672 A1    Jan. 3, 2008

(51) Int. Cl.
*C12M 1/34*    (2006.01)
*C12M 3/00*    (2006.01)

(52) U.S. Cl. .................................................. 435/288.5
(58) Field of Classification Search ................ 435/288.5
See application file for complete search history.

(56) References Cited

U.S. PATENT DOCUMENTS

| | | | | |
|---|---|---|---|---|
| 3,275,528 A | * | 9/1966 | Ainis | 435/70.1 |
| 4,674,749 A | * | 6/1987 | Shaffer et al. | 273/153 R |
| 4,975,377 A | * | 12/1990 | Key | 435/297.5 |
| 5,609,827 A | * | 3/1997 | Russell et al. | 422/102 |
| 7,186,548 B2 | * | 3/2007 | Li | 435/288.5 |
| 2004/0214313 A1 | * | 10/2004 | Zhang et al. | 435/288.4 |
| 2005/0101010 A1 | * | 5/2005 | Li | 435/304.3 |
| 2005/0244956 A1 | * | 11/2005 | Brodsky | 435/288.3 |

FOREIGN PATENT DOCUMENTS

EP    1609850 A1  *  12/2005

* cited by examiner

*Primary Examiner* — Walter D Griffin
*Assistant Examiner* — Lydia Edwards
(74) *Attorney, Agent, or Firm* — William W. Jones

(57) ABSTRACT

An apparatus for the culturing of oocytes, embryos, stem cells and cells allows the culturing of the specimens by communally growing or grouping of the specimens and maintains identification of the specimens and allows for the ease in use and location of the specimens in the apparatus. The ability to group the embryos increases cleavage rates, embryos scores and increases the likelihood of better embryos and pregnancy results. This will increase the chances of the survival and future growth or use of the specimens. The apparatus takes the form of a dish which is formed with a plurality of integral wells in which the specimens are placed. The wells or chambers may be subdivided into separate compartments which contain individual embryos or other specimens that are being cultured. The compartments will be interconnected so that the culturing media and culturing byproducts from each specimen can be shared by all of the specimens in any one well, but so that the specimens cannot migrate from one compartment to another.

6 Claims, 4 Drawing Sheets

US 7,915,034 B2

APPARATUS AND METHOD FOR CULTURING OOCYTES, EMBRYOS, STEM CELLS AND CELLS

TECHNICAL FIELD

This invention relates to an apparatus and method for culturing or growing individually identifiable cells, stem cells, immature oocytes, embryos or any portions of each in a communal environment, which allowing the interaction of fluids, nutrients or growth enhancers among the individual specimens. This invention relates to an apparatus and methods wherein individual specimens in the apparatus are kept physically separated from each other, but are permitted to share a common growth-enhancing nutrient, or share common growth byproducts, thereby resulting in an increased proficiency of the growth process. The apparatus on a larger scale will allow the progressive culturing of specimens such as embryos, stem cells and cells.

BACKGROUND ART

Human, and other animal cells, are presently cultured in suitable nutrients such as culture media for hours or days for growth, in the case of embryos, and for reproduction purposes, in the case of stem cells.

The following relates to the growth culturing of individual embryos. There are several generally practiced embryo growth procedures which are presently in use. One such growth technique involves the use of a culturing container such as a Petrie dish in which individual embryos are placed in spaced-apart locations in the culturing dish. This technique involves the initial placement of individual embryos on a growth-enhancing nutrient, and subsequently immersing each of the individual embryos in a drop of a growth-enhancing nutrient, such as culture media. Several common media are HTF, Earl's salt solution and GLOBAL culture media. The individual specimens are kept separate from each other, can be individually identified, and separately examined. Thus, the advantage of this procedure is the ability to monitor each individual embryo throughout the growth period so that there is a degree of selectivity available at the uterine-implanting stage of the process. One drawback in using this procedure relates to the fact that embryonic growth seems to be improved when the several embryos are grown in a common droplet or vial of growth-enhancing nutrient and are thus able to share each other's growth induced byproducts and this procedure does not allow the transfer of nutrients or byproducts.

Another of the generally practiced embryo growth techniques involves clustering a plurality of embryos together on a Petrie dish and immersing the cluster with a common drop of the growth-enhancing nutrient, such as culture media. Using this technique, all of the embryos in a duster are exposed to the same growth-enhancing nutrient drop and are able to share that growth-enhancing nutrient and also share their respective byproducts of the growth process. The drawback with the second technique is that one cannot distinguish one embryo from another in the cluster, in other words, each individual embryo cannot be separately monitored during the growth process. Thus, the ability to select a preferred one of the grown embryos for implanting is somewhat impaired by use of the second growth technique.

A desirable supplement for the embryo growth media is one or more growth enhancers or hormones for providing increased embryo growth, or for supplying factors that may be missing from the specimen or from the culture media. Currently, the enhancers may be obtained through the use of natural or synthetic growth hormones or from the use of stem cells to produce or give off growth hormones.

U.S. Pat. No. 6,448,069 Cecchi et al describes the separation of embryos or other specimens using what could be described as picket fences to form separate specimen compartments in a media culturing dish. One problem that is not addressed by the '069 patent is the migration of the specimens due to their size and/or weight and the possibility of them moving between the compartments. Additionally, they may not be readily discernible in the compartments by reason of the shape or configuration of the floor of the compartments.

Current products used for similar purposes are made with walls that are as vertical as practical. They do not address the fact that the embryos may measure less than ninety microns in size. This makes finding the embryos difficult in the dishes and also makes it difficult to locate an embryo f it has attached itself to a wall at some distance upwardly from the floor of the dish. The problem that arises is that the embryo is now at a different focal plane when compared to the top of the wall and the floor of the dish, and therefore is difficult to locate.

Current products of this type do not include alignment indices, which will allow the user to establish an orientation of the apparatus for viewing purposes or for the possible use with a mechanized viewing or work system.

It would be highly desirable to provide an growing method and apparatus, which would provide the ability to segregate the individual specimens, one from another, allow the addition of items such as growth factors to the apparatus while also providing the ability to allow the segregated specimens to share a common growth-enhancing cell culture media, nutrients such as growth factors and share each other's growth byproducts. It would be also highly desirable to provide an apparatus that will allow the ease in monitoring and visibility of the specimens, while keeping the specimens from migrating between compartments. It would be highly desirable to provide an apparatus that makes locating the specimens, such as embryos easier and therefore saves time and effort.

DISCLOSURE OF THE INVENTION

This invention relates to an improved method and apparatus for growing or replicating biological specimens. The method and apparatus may be used for many and various specimens which may include uterine tissues, immature oocytes, oocytes, embryos and stem cells or embryonic stem cells. The method and apparatus provide for the tracking and identification of each of the specimens as they grow or replicate. Several specimens can share a common space or configuration of wells or culturing compartment in the apparatus, which culturing compartment may include the specimens, growth-enhancing nutrient solution such as culture media, adjunct growth enhancers such as hormones and the specimen's growth byproducts. Thus the specimens may be individually monitored as to they grow, develop or replicate. The growth process is performed in a container, similar to a Petrie dish.

A plurality of compartmentalized structures may be molded in the apparatus in predetermined patterns. Each of the compartmentalized structures contains a plurality of separate compartments or sections which are sized to hold one specimen or may hold a plurality of specimens, or cell units. The compartments or sections may be separated from each other by one or more channels which form canal-like openings between each of the compartments or sections in each of the compartmentalized structures. Each of the compartmentalized structures thus allows inter compartmental migration of the growth-enhancing nutrient, culture media, fluids, growth hormones and growth byproducts that may be produced by each of the specimens disposed in one of the structures. The compartmentalized structures may be of any size necessary to hold the required number of specimens. The compartmentalized structures are preferably molded into an overall structure similar to a Petrie dish. The apparatus is molded from a suitable plastic material. The plastics preferred are plastics which exhibit minimal off gassing, low endotoxins of their structural compounds and are a material which may promote or enhance cell growth, or may be coated with cell growth materials or enhancers. The compartmentalized structures may also be structured so that the channels and connectivity is external to the compartments or sections and the compartments or sections are not directly connected by canals, channels or openings between the compartments or sections.

The following is a general description of one manner of using the apparatus of this invention for in vitro growing of fertilized embryos prior to implantation of an embryo into a female recipient's reproductive tract. As noted above, the compartmentalized specimen containing structures are preferably positioned in a Petrie dish or are an integral part of the dish itself. In such an arrangement there will be a plurality of the compartmentalized structures in the dish. These compartmentalized structures may be visibly designated by a series of identifiers such as numbers or letters, and of course their locations on the dish will be known and fixed. An area on the dish may be utilized to display information for monitoring of the specimens in the dish. Each of the compartmentalized structures will include a plurality of compartments, as, for example, two, three or four compartments. Each of the compartments will contain a separate specimen, or may contain a nutrient component such as growth hormone, growth enhancer or stem cell.

The dish can include a plurality of imbedded or molded in indices which will allow the user to orient the dish for use and also allow the user to establish fixed points of reference in the relationship to the user's workspace, microscope base. The user can thus orient the dish and then be able to locate specific points within the dish. The indices can be imbedded or molded in the bottom, or floor of the dish or in the external surface of the outer wall of the dish. This will allow greater ease in use, time savings and possible mechanical orientation for more difficult or exacting procedures. This orientation may allow the dish to be placed in an additional holding apparatus, and or placed within a controlled environment where it can be observed or worked remotely.

In the description, larger units of the apparatus will be referred to as structures, any divisions of the structures will be referred to as compartments, and the independent units will be referred to as wells.

Individual compartments in the dish will contain a raised or multiple level portions of the bottom of each compartment creating depressions or high points to cause the specimens to migrate toward the depressions of the compartments containing the specimens. Canals between the raised bottom compartments maintain the flow of fluids and material between adjacent compartments. Walls between the compartments will keep the specimens from migrating between adjacent compartments. One method to accomplish this is to make the separating walls in such a fashion that they extend above the outer walls of the compartments and extend into a layer of paraffin oil which has been dispersed in the dish. The viscosity of the paraffin oil keeps specimens, such as embryos, from moving between compartments.

It is therefore an object of this invention to provide an improved specimen growth-supporting method and apparatus which enables one to monitor the growth of individual specimens which are disposed in a growth-enhancing nutrient.

It is another object of this invention to provide a method and apparatus of the character described which enables individual embryos in a growth-enhancing nutrient to share growth byproducts of other embryos in the growth-enhancing nutrient.

It is a further object of this invention to provide a method and apparatus of the character described which will enable the user to readily locate individual embryos that are within the apparatus.

It is yet another object of this invention to provide a method and apparatus of the character described which will enable the user to establish a directional orientation of the apparatus which will allow the apparatus to be used with mechanical instruments and to readily find specific points of reference and therefore be able to find the specimens that are within the apparatus.

BRIEF DESCRIPTION OF THE DRAWINGS

These and other objects and advantages of the invention will become more readily apparent from the following detailed description of the invention, when taken in conjunction with the accompanying drawings in which.

DETAILED DESCRIPTION OF THE INVENTION

Figure 1:
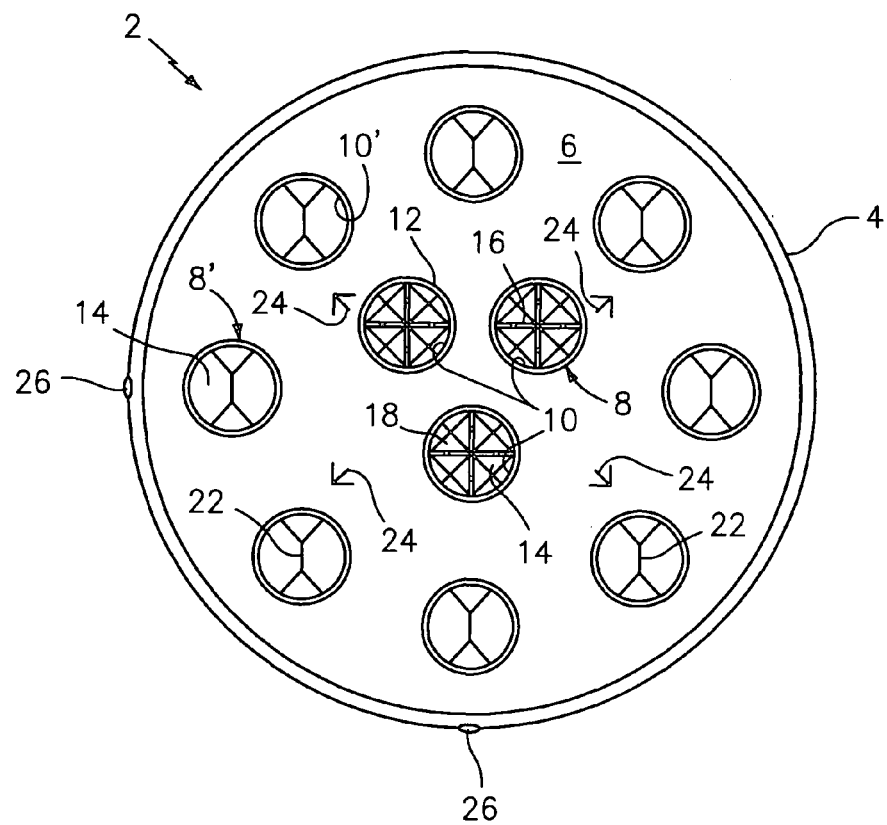
FIG. 1 is a top plan view of one embodiment of a specimen culturing dish formed in accordance with this invention.
Figure 2:
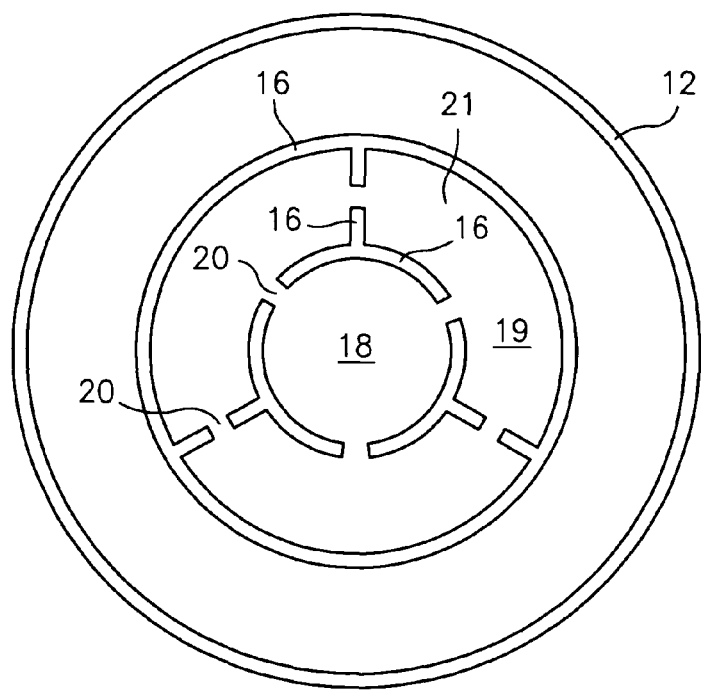
FIG. 2 is a top plan view of one of the embryo growth compartments contained in the specimen sample culturing dish of FIG. 1 which includes several internal compartmentalized embryo growth structures.

Referring now to FIGS. 1 and 2 there is shown an oocyte, embryo and stem cell specimen growth container, denoted generally by the numeral 2 which is formed in accordance with this invention. The container 2 has an outer wall 4 and a bottom wall 6. The bottom wall 6 is flat, and has a small raised portion below the outer wall 4 which will keep the bottom wall 6 slightly elevated above a surface it may be placed on, thereby keeping the bottom wall 6 from being scratched by the surface it is placed on. Thus, in the areas where the user needs to maintain clear ocular views, they will be maintained. Molded into the container 2 are a plurality of structures 8 that form compartments 10 which are used for the culturing of the specimens which can be, for example, embryos. The structures 8 include an outer wall 12 and a recessed formed bottom wall or floor 14, and can include inner walls or separators 16 that create individual chambers 18 in each compartment 10. The recessed bottom walls 14 allow the user to more readily locate the embryos under magnification in the compartments 10 and chambers 18. The container 2 measures typically fifty five cm. in diameter and has an outer wall 4 which is typically one cm in height The multiple culturing compartments 10 measure typically 1.2 cm in diameter and their exterior walls 12 typically measure two mm in height. The interior walls or separators 16 are slightly taller and typically measure 2.2 mm in height.

As shown in FIG. 2, within these separators or walls 16 are spaces or channels 20 which will allow the fluids to flow between the culturing compartments 18 and 19. The interior walls or separators 16 are taller than the outer wall 12 of the culturing compartments 10 so that when the dish 2 is flooded with mineral oil or paraffin oil which overlays the media in the compartments, the taller walls 16 will penetrate the oil layer and, due to the viscosity of the oil, the embryos will not migrate through this layer and thus cannot migrate into a different compartment 18.

The dish 2 may contain a plurality of smaller structures 8' which form additional compartments 10'. These structures 8' may be evenly placed about the dish 2 and are typically eight mm in diameter and have walls which are typically two mm in height. These structures 8' take the form of wells which can be used as reservoirs of culture media, for the holding or washing of embryos or specimens, or for the individual culturing of embryos or specimens. The floor 14 of the wells 8' is contoured so as to create a low point and/or depression 22 in the floor 14. The depressions 22 allow the embryos or other specimens to settle into known locations in the wells 8' to simplify locating of the specimens when viewed under magnification. The depressions 22 in the culturing wells 8' are all the same viewing distance and at the same ocular setting of the microscope so as to allow the user to move among the culturing compartment wells 8' and floor 6 of the dish 2 without changing the setting of the microscope. During use, the culturing compartments 18 and wells 8' will be immersed with culture media. The entire dish 2 can then be flooded with paraffin oil, or mineral oil to keep the medium from evaporating, prevent absorption of air contaminants, and to utilize the structural height of the inner compartment walls or separators 16 to keep embryos or other specimens from migrating among compartments 18.

Embedded or molded into floor 6 of the dish 2 are orientation indices 24. These indices 24 allow the user to orient the dish 2 and simplify locating of the specimens. The indices 24 will also allow the dish 2 to be set up on the microscope stage in the same orientation and may be used to establish the same orientation each time the specimens are viewed. The dish 2 can also have external indices 26 imbedded in or on the outer wall 4 of the dish 2 for this purpose.

As noted above, FIG. 2 is a top plan view of an oocyte, embryo or stem cell growth compartment 12. The walls 16 separate the compartment 12 into a central chamber 18 for containing the specimen being cultured which is surrounded by an inner annular trough 19. The walls 16 may be continuous and uninterrupted, or they may be segmented with the segments being separated by gaps in the walls 16. The trough 19 may hold addition fluids for use in culturing the specimens. Within the walls 16 that separate the chambers 18 and 19 are openings 20 which will allow the flow of liquids between and among the chambers 18 and 19. The areas of chambers 18 and 19 may be used to hold specimens, and in this example, will allow fluid flow between the four separate chambers.

Figure 3:
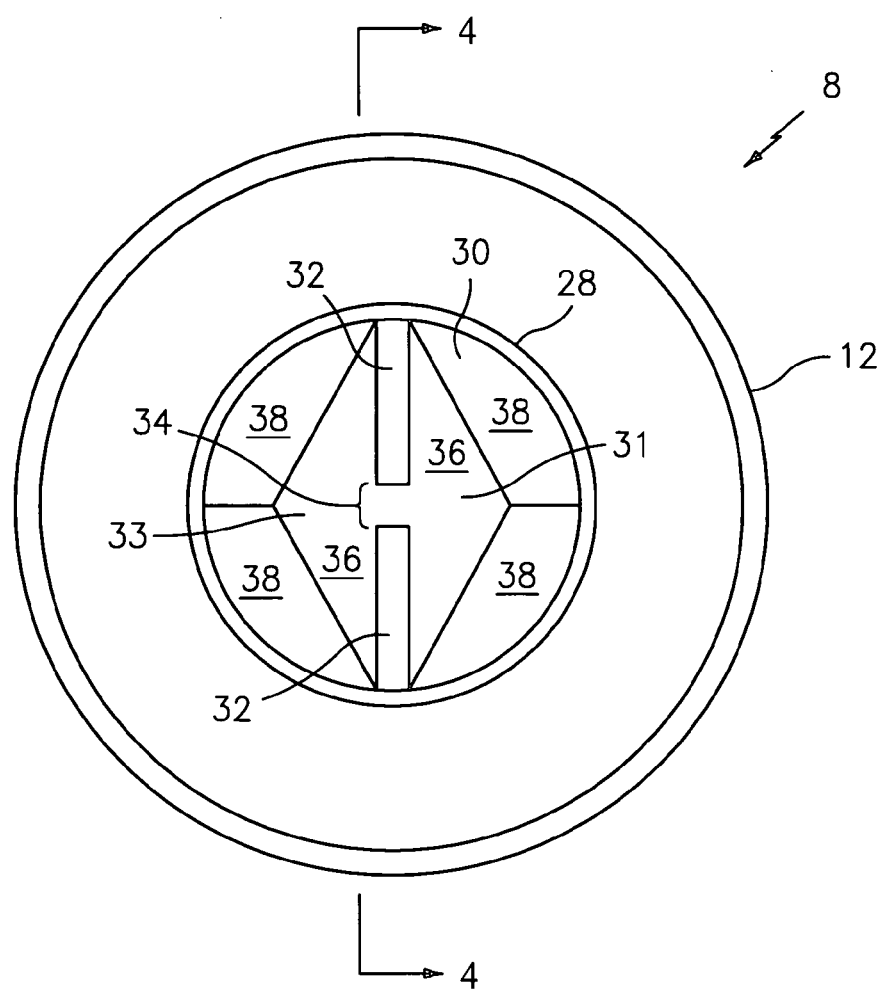
FIG. 3 is a top plan view similar to FIG. 2 but showing another variation of an internally compartmentalized embryo growth compartment.
Figure 4:
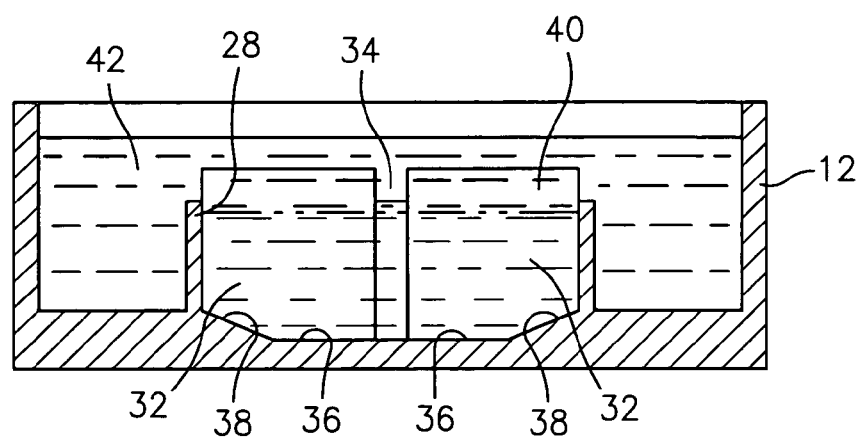
FIG. 4 is a sectional view of the compartment shown in FIG. 3 taken along line 4-4 of FIG. 3.

Referring now to FIGS. 3 and 4, there is shown a modification of one of the specimen compartments 8. The compartment 8 contains an outer wall 12 and an inner wall 28. The inner wall 28 forms a chamber 30 which is segregated into two halves 31 and 33 by a wall 32. An opening 34 separates the wall 32 into two spaced-apart sections. The opening 34 allows fluids to move between the two halves 31 and 33 of the chamber 30. The opening 34 is small enough to prevent embryos from moving from one half 31 to the other half 33 of the chamber 30, thereby allowing the chamber 30 to be used to culture two embryos which can share the culturing fluids that are put in the chamber 30, and also share growth byproducts which are produced by each of the embryos during the culturing period. The opening 34 may also contain a membrane to allow fluids but not specimens to move. Specimens may also be placed in areas 18, 19, 24 and 26. This will enable these specimens to share nutrients and byproducts in all four of these areas. Specimens may also be placed in areas 19, 24 and 26 with special ingredients, such as growth factors, being placed in area 18. This will allow specimens in these three areas to share amongst each other.

As shown in FIG. 4, the bottom wall of the chamber 30 is a compound structure which has a central lowest flat horizontal portion 36 and outer flat downwardly angled portions 38. Embryos which are cultured in the chamber sections 31 and 33 will thus settle down onto the lowest portion 36 of the bottom wall of the chamber 30 where they can be easily located for visual inspection during the culturing period. FIG. 4 also shows the use of taller walls 32 and opening 34 to keep the embryos contained in the individual chamber sections 31 and 33 and prevent them from migrating from one chamber section to the other. As shown in FIG. 4, a culture media 40 is placed in the chamber 30. The compartment 8 is then flooded with paraffin oil or mineral oil 42. The oil 42 overlays or sits on top of the media 40. The walls 32 extend up into the layer of oil 42. Due to the viscosity of the oil 42, embryos or other specimens cannot migrate or move from one chamber section 31 to the other chamber section 33. Thus, the individual specimens which are being cultured are "trapped" in their respective culturing chamber sections 31 and 33 during the culturing procedure. The upper section of walls 32 are immersed in the oil layer 42, above the wall 28. This embodiment illustrates the ability of media, nutrients, fluids and growth hormones or growth byproducts to flow through the opening 34 to be shared by specimens in chamber sections 31 and 32. The opening 34 is of a size which will not allow the specimens to move through the opening 34.

Figure 5:
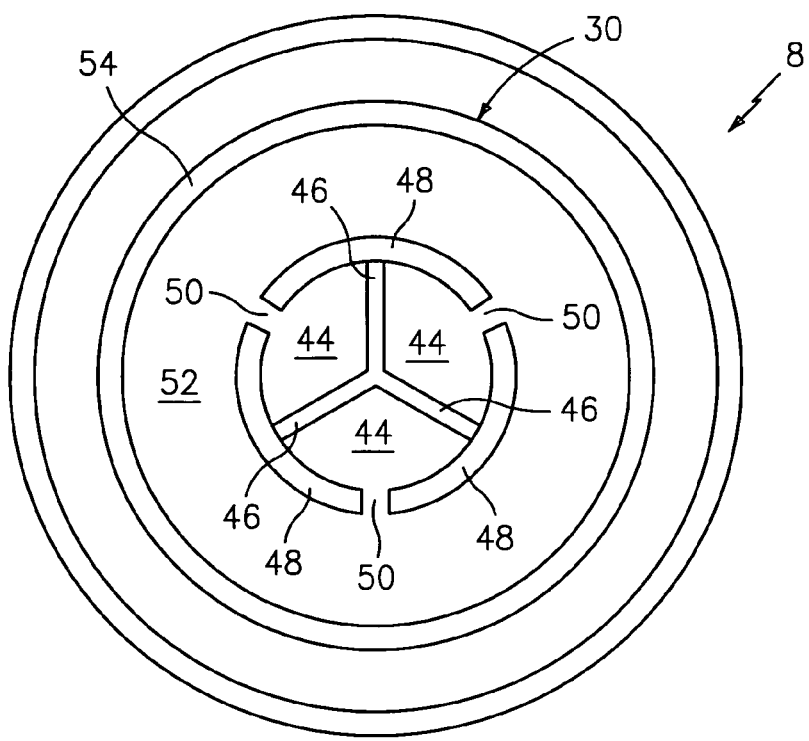
FIG. 5 is a top plan view similar to FIG. 3 but showing yet another variation of an internally compartmentalized embryo growth compartment.

FIG. 5 shows a modification of a culturing compartment 8 which includes a culturing chamber 30 having chamber sections 44 that are separated from each other by walls 46 that block direct media flow between the culturing chamber sections 44. Each of the sections 44 is bounded by an outer wall 48 which has openings 50 for each of the sections 44. An outer chamber 52 bounded by an outer wall 54 surrounds the sections 44. The culturing media can be placed in the outer chamber 52 and will be able to migrate into the sections 44 through the openings 50. The specimens to be cultured will be placed in the sections 44 and will be able to share the culturing media and culturing byproducts indirectly by reason of the openings 50. The openings 50 will be too small to allow any of the specimens to move from one of the sections 44 to another or may utilize a membrane to keep the specimens from migrating. Thus the specimens will be restricted to their respective sections 44 but will still be able to share the culturing media and culturing byproducts that each produces via the outer chamber 52. Not shown in this figure is the raised walls or depression of the floor of the compartments, but these items can be used in this configuration also.

Figure 6:
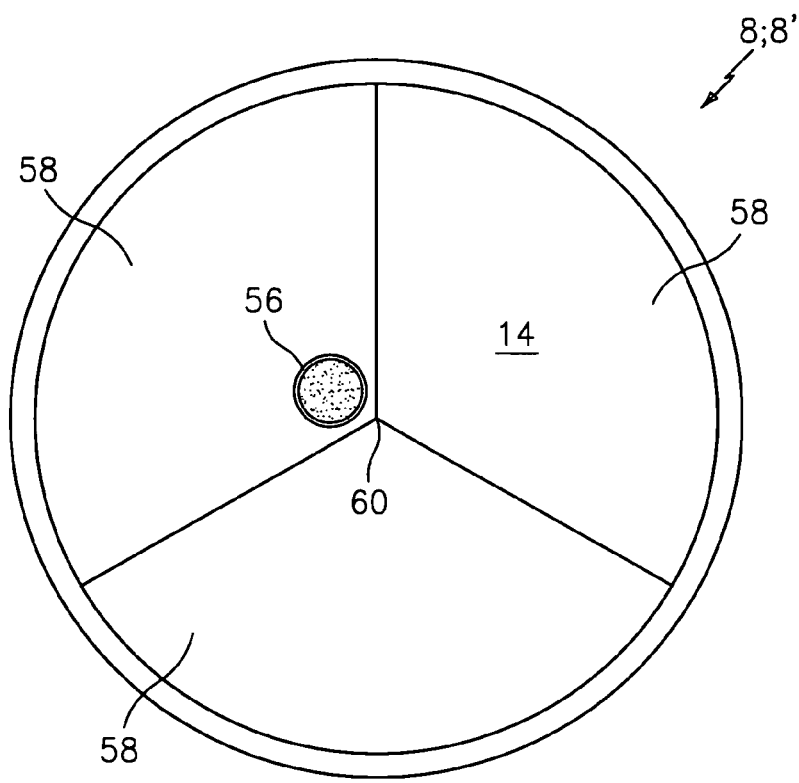
FIG. 6 is a top plan view of an embryo growth compartment formed in accordance with this invention and showing how an individual embryo will settle to a predetermined location in the compartment which position is dictated by the configuration of the bottom wall of the compartment.

FIG. 6 is a plan view of a culturing compartment 8 or 8' showing how one version of the contoured floor 14 of the compartment serves to place an embryo 56, or other specimen, in a predetermined location on the compartment floor 14. In this embodiment, the floor 14 has three segments 58 which are planar and slope at the same angle downwardly to a central point 60. This configuration will cause the embryo 56 to migrate toward the central point 60 where it can be readily located visually with a microscope or other optical instrument so that the stages of development of the embryo 56 can be monitored during the culturing cycle. The slope of the floor segments 58 creates a known depth of the point 60 so that the focal point of the viewing instrument can be preset so that each of the compartments 8 or 8' in a culturing dish can be monitored for embryo stage development without having to refocus the viewing instrument.

Figure 7:
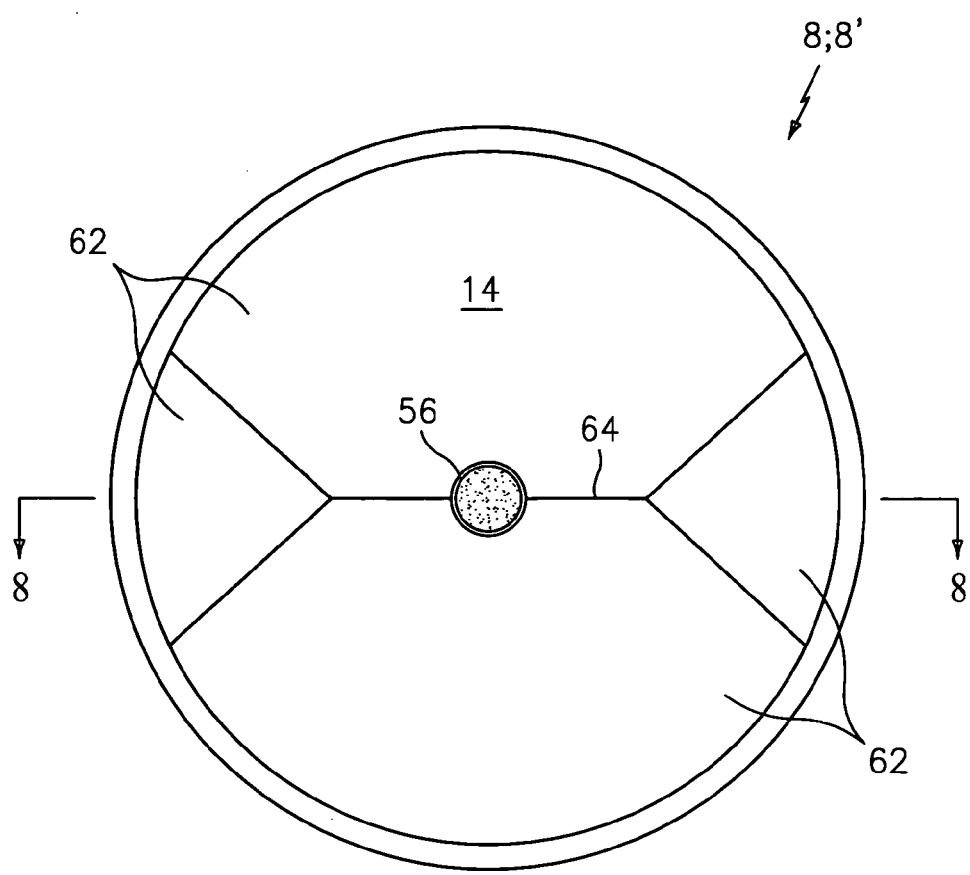
FIG. 7 is a top plan view of yet another configuration of an embryo growth compartment showing how an embryo settles to a predetermined location on the bottom wall of the compartment.
Figure 8:
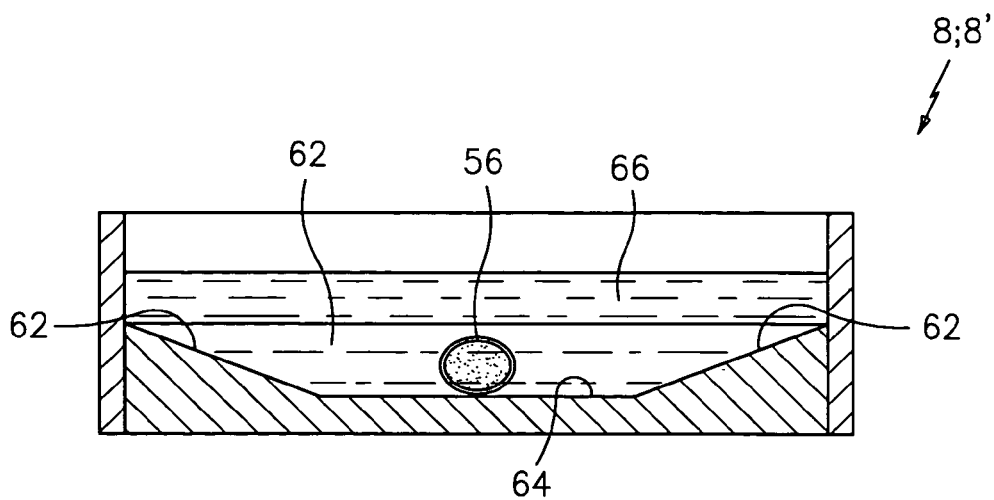
FIG. 8 is a sectional view of the compartment taken along line 8-8 of FIG. 7.

Referring now to FIGS. 7 and 8 there is shown therein a culturing compartment 8 or 8' which is similar to that shown in FIG. 6, but which has a different bottom floor 14 contour configuration than that shown in FIG. 6. The bottom floor 14 has four planar segments 62 which slope downwardly to form a linear central low location 64 into which an embryo 56 or other specimen being cultured will settle. This configuration will cause the embryo 56 to migrate toward the central location 64 where it can be readily located visually with a microscope or other optical instrument so that the stages of development of the embryo 56 can be monitored during the culturing cycle. The slope of the floor segments 62 creates a known depth of the location 64 so that the focal point of the viewing instrument can be preset so that each of the compartments 8 or 8' in a culturing dish can be monitored for embryo stage development without having to refocus the viewing instrument. The sloped floor segments 62 also will result in the dispersal of debris along the line 64 so as to allow the specimen to be debris-free. As shown in FIG. 8, the embryo 56 will be covered by a culturing media and/or oil layer 66 during the culturing procedure.

It will be readily appreciated that the cell culturing apparatus of this invention will allow individual specimens being cultured in the apparatus to share nutrients, and perhaps even more importantly, to share growth byproducts produced by each of the specimens. This result is accomplished while physically isolating each specimen from each of the other specimens in the apparatus. Additionally, each specimen in the apparatus can be monitored visually or with an appropriate monitoring instrument at a predetermined focal plane in the apparatus. The apparatus can also include visible indicia which enable a technician to spatially orient the apparatus and identify individual specimens in the apparatus. The apparatus preferably takes the form of a specimen culturing dish which has individual chambers that can be subdivided into separate compartments.

Since many changes and variations of the disclosed embodiment of the invention may be made without departing from the inventive concept, it is not intended to limit the invention except as required by the appended claims.

What is claimed is:

1. A biological specimen culturing container adapted for culturing biological specimens such as oocytes, embryos, stem cells, tissue cells and the like, said culturing container including:
   a) a bottom wall and an outermost side wall;
   b) a plurality of specimen-culturing chambers in said container, each of said chambers having an outermost chamber side wall which separates each chamber from all of the other chambers; and
   c) some of said chambers being subdivided into individual interconnected compartments for receiving the specimens to be cultured, said compartments being interconnected in a manner which will allow each specimen in each of said compartments to share culturing media and specimen growth byproducts with specimens in each of the other compartments in each of said subdivided chambers; and
   d) said compartments in said chambers being formed by inner walls and said compartments being interconnected by openings in said inner walls.

2. The container of claim 1 wherein said outermost chamber side walls are essentially circular and some of said inner walls are concentric with said outermost chamber side walls.

3. The container of claim 2 wherein said inner walls also include radial walls which extend between adjacent ones of said concentric inner walls.

4. The container of claim 3 wherein some of said radial walls and said concentric inner walls include openings therein.

5. A biological specimen culturing container adapted for culturing biological specimens such as oocytes, embryos, stem cells, tissue cells and the like, said culturing container including:
   a) a bottom wall and an outermost side wall;
   b) a plurality of specimen-culturing chambers in said container, each of said chambers having an outermost chamber side wall which separates each chamber from all of the other chambers;
   c) at least some of said chambers having bottom walls which are contoured in a manner which will cause each specimen in each of such chambers to settle into a lowermost location in such chambers which location is in a predetermined focal plane relative to optical instruments used to visually monitor the specimens;
   d) interior walls in some of said chambers which subdivide the chambers having said interior walls into separate compartments; and
   e) said compartments being interconnected by openings in some of said interior walls.

6. The container of claim 5 wherein said openings are smaller than the specimens so that the specimens cannot migrate from one compartment to another through said openings.

* * * * *